(12) United States Patent
Watanabe et al.

(10) Patent No.: US 11,172,025 B2
(45) Date of Patent: *Nov. 9, 2021

(54) SERVER APPARATUS, ODOR SENSOR DATA ANALYSIS METHOD, AND COMPUTER-READABLE RECORDING MEDIUM

(71) Applicant: NEC CORPORATION, Tokyo (JP)

(72) Inventors: Junko Watanabe, Tokyo (JP); Riki Eto, Tokyo (JP); Hidetaka Hane, Tokyo (JP); Shigeo Kimura, Tokyo (JP); Shintarou Tsuchiya, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/753,279

(22) PCT Filed: Oct. 2, 2018

(86) PCT No.: PCT/JP2018/036956
§ 371 (c)(1),
(2) Date: Apr. 2, 2020

(87) PCT Pub. No.: WO2019/069959
PCT Pub. Date: Apr. 11, 2019

(65) Prior Publication Data
US 2020/0336543 A1 Oct. 22, 2020

(30) Foreign Application Priority Data
Oct. 3, 2017 (JP) .............................. JP2017-193902

(51) Int. Cl.
*H04L 29/08* (2006.01)
*G01N 33/00* (2006.01)
(Continued)

(52) U.S. Cl.
CPC ......... *H04L 67/12* (2013.01); *G01N 33/0031* (2013.01); *G01N 33/0062* (2013.01);
(Continued)

(58) Field of Classification Search
CPC . H04L 67/12; H04L 67/2895; H04L 67/2828; G01N 33/0031; G01N 33/0062
See application file for complete search history.

(56) References Cited

U.S. PATENT DOCUMENTS

2011/0119769 A1* 5/2011 Homer ................ G06F 16/3344
726/27
2013/0066349 A1* 3/2013 Fink ....................... A61B 5/445
606/169
(Continued)

FOREIGN PATENT DOCUMENTS

JP 2008-237718 A 10/2008
JP 5582803 B2 9/2014
(Continued)

OTHER PUBLICATIONS

MSS alliance launched to set de facto standard for odor-sensing systems—aiming to establish basic elements of MSS technology towards practical use—[online], Sep. 29, 2015, NEC Corp., [viewed on Sep. 1, 2015], Internet <URL: http://jpn.nec.com/press/201509/20150929_01.html>.
(Continued)

*Primary Examiner* — Arvin Eskandarnia
*Assistant Examiner* — Chhian (Amy) Ling
(74) *Attorney, Agent, or Firm* — Sughrue Mion, PLLC

(57) ABSTRACT

A terminal apparatus 20 includes a sensor data collection unit 21 that collects sensor data from an odor sensor 40 that outputs the sensor data in reaction to a plurality of types of odors, an analyzer acquisition unit 22 that, in the case where an analyzer capable of analyzing a designated odor analysis
(Continued)

target is transmitted thereto from a server apparatus 10 that holds a plurality of analyzers for analyzing odor analysis targets by analyzing the sensor data, acquires the analyzer transmitted thereto, an analysis execution unit 23 that executes analysis processing of the designated odor analysis target, by applying the acquired analyzer to the collected sensor data, and an analysis result holding unit 24 that holds information indicating a result of the analysis processing.

16 Claims, 11 Drawing Sheets

(51) Int. Cl.
    *G16Y 10/90*    (2020.01)
    *G16Y 40/20*    (2020.01)

(52) U.S. Cl.
    CPC ...... *H04L 67/2828* (2013.01); *H04L 67/2895* (2013.01); *G01N 2033/0068* (2013.01); *G16Y 10/90* (2020.01); *G16Y 40/20* (2020.01)

(56) References Cited

U.S. PATENT DOCUMENTS

2016/0363582 A1\* 12/2016 Blackley .............. G01N 33/497
2017/0010664 A1\* 1/2017 Tanaka .................... G06F 3/015

FOREIGN PATENT DOCUMENTS

| | | |
|---|---|---|
| JP | 6121014 B2 | 4/2017 |
| JP | 2017-513536 A | 6/2017 |

OTHER PUBLICATIONS

International Search Report of PCT/JP2018/036956 dated Dec. 25, 2018 [PCT/ISA/210].

Written Opinion of the International Searching Authority dated Dec. 25, 2018, in International Application No. PCT/JP2018/036956.

\* cited by examiner

Fig.5

| ANALYZER ID | FEATURE AMOUNT EXTRACTION MODULE ID | ANALYSIS TARGET INFORMATION | ANALYSIS ACCURACY | COMPATIBLE TEMPERATURES | INDEX LIST |
|---|---|---|---|---|---|
| ANALYZER 1 | MODULE 1 | A,B,C | 90% | 25°C-30°C | i0,...i99 |
| ANALYZER 2 | MODULE 2 | A,B,C | 60% | 15°C-40°C | j0,...j49 |
| ANALYZER 3 | MODULE 3 | C,D,E,F | 90% | 20°C-35°C | k0,...k119 |
| ANALYZER 4 | MODULE 4 | C,D,E,F | 70% | 0°C-15°C | h0,...h79 |
| ... | ... | ... | ... | ... | ... |

SERVER APPARATUS, ODOR SENSOR DATA ANALYSIS METHOD, AND COMPUTER-READABLE RECORDING MEDIUM

CROSS REFERENCE TO RELATED APPLICATIONS

This application is a National Stage of International Application No. PCT/JP2018/036956, filed Oct. 2, 2018, claiming priority to Japanese Patent Application No. 2017-193902, filed Oct. 3, 2017, the contents of all of which are incorporated herein by reference in their entirety.

TECHNICAL FIELD

The present invention relates to a server apparatus and an odor sensor data analysis method that are for performing substance detection using an odor sensor capable of detecting substances in the atmosphere, and, furthermore, relates to a computer-readable recording medium that includes a program recorded thereon for realizing the apparatus and method.

BACKGROUND ART

Heretofore, odor sensors have been used in order to detect specific odors (e.g., refer to Patent Documents 1 and 2). An odor sensor detects a specific odor, by detecting an airborne chemical substance that produces a specific odor with a sensor element. Also, a metal oxide and an organic semiconductor thin film are given as examples of a sensor element. With such a sensor element, conductivity changes when a specific chemical substance adheres thereto, thus enabling the specific chemical substance to be detected.

Incidentally, with conventional odor sensors, there is a problem in that detectable chemical substances are fixed, and thus the odors that are detected are also fixed, resulting in a lack of versatility. In response, a Membrane-type Surface stress Sensor (MSS) that is able to detect a wide range of substances has been newly proposed in recent years (refer to Non-Patent Document 1).

An MSS is usually constituted by two or more MSS elements. Each MSS element includes a circular portion provided with a sensitive membrane, a frame surrounding the circular portion, and a plurality of bridges for coupling the circular portion to the frame. A piezoresistive element is embedded in each bridge. In such a configuration, the circular portion deforms due to stress occurring in the sensitive membrane when a substance sticks to the sensitive membrane, resulting in stress being applied to the bridges. As a result, the electrical resistance of the piezoresistive elements embedded in the bridges changes greatly, thus enabling the substance stuck to the sensitive membrane to be detected from the resistance value.

Also, with an MSS, the material of the sensitive membrane differs for every MSS element, but this does not necessarily mean that the substance that sticks to each MSS element is fixed to one type. The material of the sensitive membrane of each MSS element is configured such that the pattern of the output data of the entire MSS that is obtained by compositing the output data of the respective MSS elements differs according to the substance. Thus, with an MSS, it becomes possible to detect multiple types of odors, by learning output patterns and creating analyzers, for every analysis target, though machine learning in advance.

Note that there is also a technique that involves using a plurality of odor sensors having different characteristics including odor sensors other than an MSS, performing analysis through machine learning by combining data from the respective odor sensors, and generating odor an analyzer for every target.

LIST OF RELATED ART DOCUMENTS

Patent Document

Patent Document 1: Japanese Patent No. 6121014
Patent Document 2: Japanese Patent No. 5582803

Non-Patent Document

Non-Patent Document 1: MSS alliance launched to set de facto standard for odor-sensing systems—aiming to establish basic elements of MSS technology towards practical use.

SUMMARY OF INVENTION

Problems to be Solved by the Invention

Incidentally, since the analyzer differs for every analysis target in the case of such odor sensors, a large number of analyzers need to be implemented in an apparatus provided with an odor sensor, in the case of performing detection of a large number of types of odors. Also, a characteristic of an MSS is that, even with the same analysis target, the behavior of the sensor data changes when environmental conditions such as temperature and humidity change. Thus, in order to respond to a variety of environmental conditions, it is also necessary to implement an analyzer for every environmental condition.

On the other hand, in order to enable users to easily perform odor detection with an odor sensor, the device needs to be of a size that is handy for carrying around, and, furthermore, of a size attachable to a smartphone. However, implementing a large number of analyzers becomes difficult when attempting to achieve device miniaturization. Thus, with a device provided with a conventional odor sensor, detecting a large number of types of odors while responding to environmental conditions is extremely difficult.

An example object of the invention is to provide a server apparatus, an odor sensor data analysis method and a computer-readable recording medium that, in the case where substance detection is performed using an odor sensor whose odor analysis target is not fixed, can enable utilization of an analyzer adapted to the situation, without implementing a large number of analyzers.

Means for Solving the Problems

A server apparatus according to an example aspect of the invention is configured to be communicably connected to a terminal apparatus for collecting sensor data from an odor sensor that outputs the sensor data in reaction to a plurality of types of odors and performing analysis of an odor analysis target, the server apparatus comprising:

an analyzer holding unit configured to hold a plurality of analyzers for analyzing specific odor analysis targets by analyzing the sensor data;

an analyzer selection unit configured to select an analyzer capable of analyzing a designated odor analysis target, from among the plurality of analyzers; and an analyzer transmission unit configured to transmit the selected analyzer to the terminal apparatus.

A terminal apparatus according to an example aspect of the invention is for collecting sensor data from an odor sensor that outputs the sensor data in reaction to a plurality of types of odors and performing analysis of an odor analysis target to carry out:

a sensor data collection unit configured to collect the sensor data;

an analyzer acquisition unit configured to, in a case where an analyzer capable of analyzing a designated odor analysis target is transmitted to the terminal apparatus from a server apparatus that holds a plurality of analyzers for analyzing specific odor analysis targets by analyzing the sensor data, acquire the analyzer transmitted thereto;

an analysis execution unit configured to execute analysis processing of the designated odor analysis target, by applying the acquired analyzer to the collected sensor data; and an analysis result holding unit configured to hold information indicating a result of the analysis processing.

Also, an odor sensor data analysis method according to an example aspect of the invention uses a terminal apparatus for collecting sensor data from an odor sensor that outputs the sensor data in reaction to a plurality of types of atmospheric substances and performing analysis of an odor analysis target and a server apparatus configured to be communicably connected to the terminal apparatus, the method comprising:

(a) a step of, with the terminal apparatus, collecting the sensor data;

(b) a step of, with the server apparatus, selecting an analyzer capable of analyzing a designated odor analysis target, from among a plurality of analyzers for analyzing specific odor analysis targets by analyzing the sensor data;

(c) a step of, with the server apparatus, transmitting the selected analyzer to the terminal apparatus;

(d) a step of, with the terminal apparatus, acquiring the analyzer transmitted thereto from the server apparatus;

(e) a step of, with the terminal apparatus, executing analysis processing of the designated odor analysis target, by applying the acquired analyzer to the collected sensor data; and (f) a step of, with the terminal apparatus, holding information indicating a result of the analysis processing.

Furthermore, a computer-readable recording medium according to an example aspect of the invention includes a program recorded thereon, the program including instructions that cause a computer configured to be communicably connected to a terminal apparatus for collecting sensor data from an odor sensor that outputs the sensor data in reaction to a plurality of types of atmospheric substances and performing analysis of an odor analysis target to carry out:

(a) a step of holding a plurality of analyzers for analyzing specific odor analysis targets by analyzing the sensor data;

(b) a step of selecting an analyzer capable of analyzing a designated odor analysis target, from among the plurality of analyzers; and (c) a step of transmitting the selected analyzer to the terminal apparatus.

Furthermore, a computer-readable recording medium according to an example aspect of the invention includes a program recorded thereon, the program including instructions that cause a computer for collecting sensor data from an odor sensor that outputs the sensor data in reaction to a plurality of types of odors and performing analysis of an odor analysis multi-design to carry out:

(a) a step of collecting the sensor data;

(b) a step of, in a case where an analyzer capable of analyzing a designated odor analysis target is transmitted to the terminal apparatus from a server apparatus that holds a plurality of analyzers for analyzing specific odor analysis targets by analyzing the sensor data, acquiring the analyzer transmitted thereto;

(c) a step of executing analysis processing of the designated odor analysis target, by applying the acquired analyzer to the collected sensor data; and (d) a step of holding information indicating a result of the analysis processing.

Advantageous Effects of the Invention

As described above, according to the invention, in the case where substance detection is performed using an odor sensor whose analysis target is not fixed, it becomes possible to utilize an analyzer adapted to the situation, without implementing a large number of analyzers.

BRIEF DESCRIPTION OF THE DRAWINGS

FIG. 5 is a diagram showing an example of a table that is used in selection of an analyzer and determination of pre-processing in the example embodiment of the invention.

EXAMPLE EMBODIMENTS (Example Embodiment)

Hereinafter, a server apparatus, a terminal apparatus, an odor sensor data analysis method and a program according to an example embodiment of the invention will be described, with reference to FIGS. 1 to 11.

[Apparatus Configuration]

Figure 1:
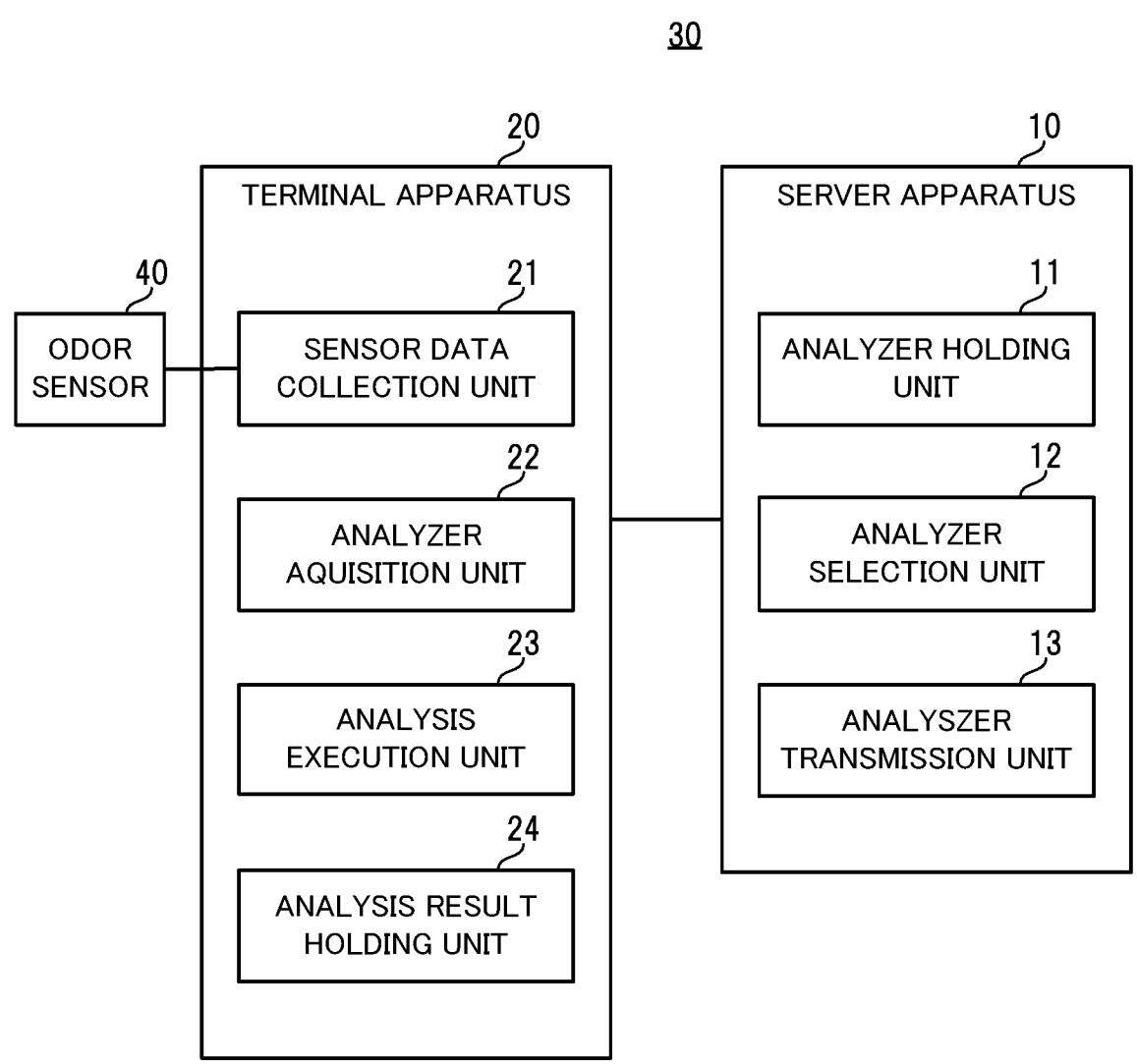
FIG. 1 is a block diagram showing schematic configurations of a server apparatus and a terminal apparatus according to an example embodiment of the invention.

Initially, schematic configurations of the server apparatus and the terminal apparatus according to the example embodiment will be described. FIG. 1 is a block diagram showing schematic configurations of the server apparatus and the terminal apparatus according to the example embodiment of the invention.

A server apparatus 10 and a terminal apparatus 20 shown in FIG. 1 constitute a system 30 for detecting odors using an odor sensor 40. The odor sensor 40 that is used in the example embodiment is a sensor that outputs sensor data in reaction to a plurality of types of odors. Also, with the odor sensor 40, it becomes possible to detect various odor analysis targets, by using a number of analyzers that analyze specific odor analysis targets, based on sensor data.

In the example embodiment, "odor" includes not only scents and smells that people experience with their sense of smell but also gas molecules that are produced from the expiration or excretion of organisms and chemical composition elements (gas molecules, etc.) included in the outside air that reflect the situation of the target whose analysis is sought, such as the illness of an organism or the degradation of a structure.

Also, "odor analysis targets" include the actual odors that serve as an analysis target, and, furthermore, the contraction of diseases that produces odors, the degree of ripeness of fruit that likewise produces odors, the degree of degradation of structures that likewise produces odors.

As shown in FIG. 1, the server apparatus 10 and the terminal apparatus 20 are communicably connected to each other. The terminal apparatus 20 collects sensor data (henceforth, also referred to as "odor sensor data") from the odor sensor 40, and analyze odors. The server apparatus 10 transmits an analyzer required in analysis processing on an odor analysis target to the terminal apparatus 20.

Also, as shown in FIG. 1, the server apparatus 10 includes an analyzer holding unit 11, an analyzer selection unit 12, and an analyzer transmission unit 13. Of these, the analyzer holding unit 11 holds a plurality of analyzers for analyzing specific odor analysis targets by analyzing sensor data.

The analyzer selection unit 12 selects an analyzer capable of analyzing a designated odor analysis target, from among the plurality of analyzers. Also, the analyzer transmission unit 13 transmits the analyzer selected by the analyzer selection unit 12 to the terminal apparatus 20.

Also, as shown in FIG. 1, the terminal apparatus 20 includes a sensor data collection unit 21, an analyzer acquisition unit 22, an analysis execution unit 23, and an analysis result holding unit 24. Of these, the sensor data collection unit 21 collects sensor data that is output by the odor sensor 40.

The analyzer acquisition unit 22, in the case where an analyzer capable of analyzing the designated odor analysis target is transmitted to the terminal apparatus 20 from the server apparatus 10 which holds a plurality of analyzers for analyzing specific odor analysis targets by analyzing sensor data, acquires the analyzer transmitted thereto.

The analysis execution unit 23 executes analysis processing of the designated odor analysis target, by applying the analyzer acquired by the analyzer acquisition part 22 to the sensor data collected by the sensor data collection unit 21. The analysis result holding unit 24, when analysis processing is executed by the analysis execution unit 23, holds information indicating a result of the analysis processing.

In this way, in the example embodiment, the odor sensor 40 is utilized by edge computing that includes the server apparatus 10 and the terminal apparatus 20. Also, an analyzer suitable for analysis of the odor analysis target is sent to the terminal apparatus 20 from the server apparatus 10. Thus, the terminal apparatus 20 is able to perform analysis processing, using an appropriate analyzer, even when a large number of analyzers are not provided in advance. In other words, according to the example embodiment, it becomes possible to utilize an analyzer adapted to the situation, without implementing a large number of analyzers, in the case of performing odor analysis using an odor sensor whose analysis target is not fixed.

Figure 2:
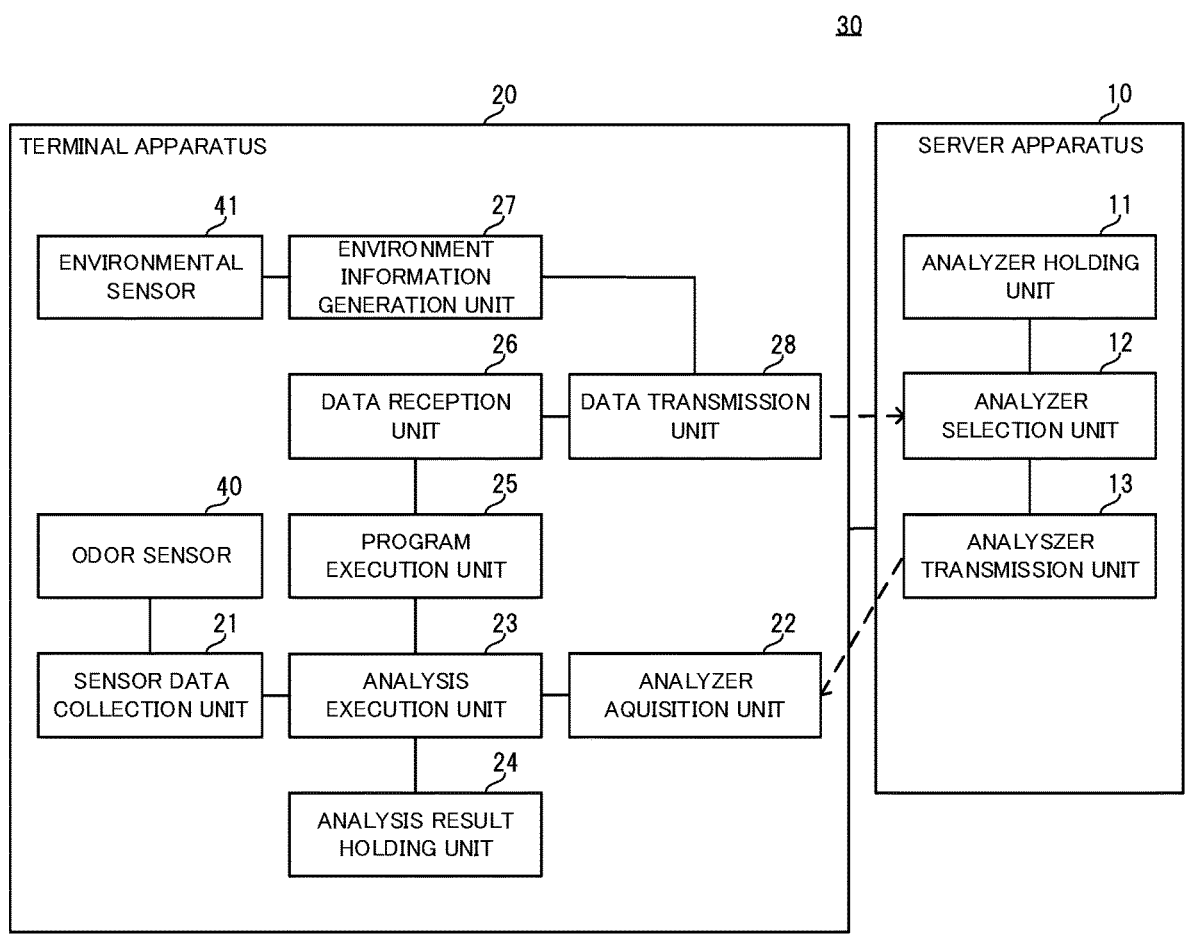
FIG. 2 is a block diagram more specifically showing the configurations of the server apparatus and the terminal apparatus according to the example embodiment of the invention.
Figure 3:
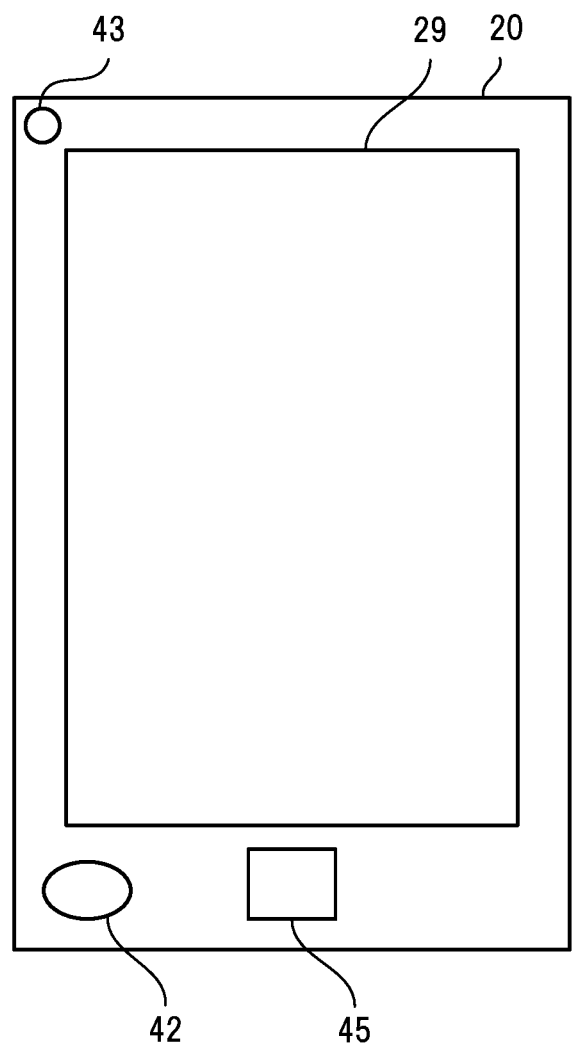
FIG. 3 is a diagram showing an external appearance of the terminal apparatus according to the example embodiment of the invention.
Figure 4:
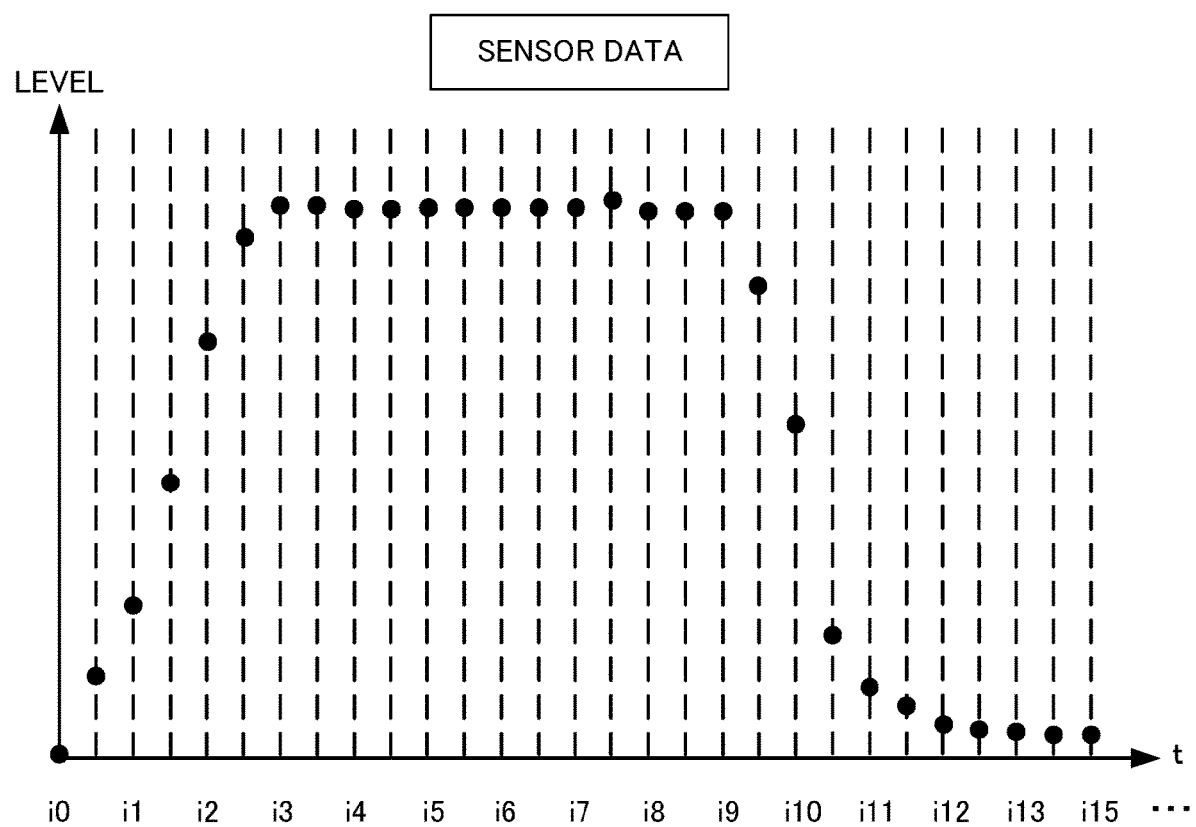
FIG. 4 is a diagram showing an example of sensor data that is output by an odor sensor in the example embodiment of the invention.
Figure 6A:
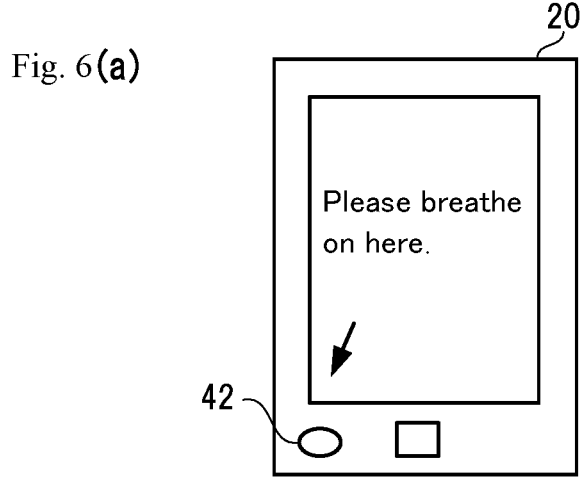
FIGS. 6(*a*) to 6(*c*) show an example of information that is displayed on a screen of the terminal apparatus.
Figure 6B:
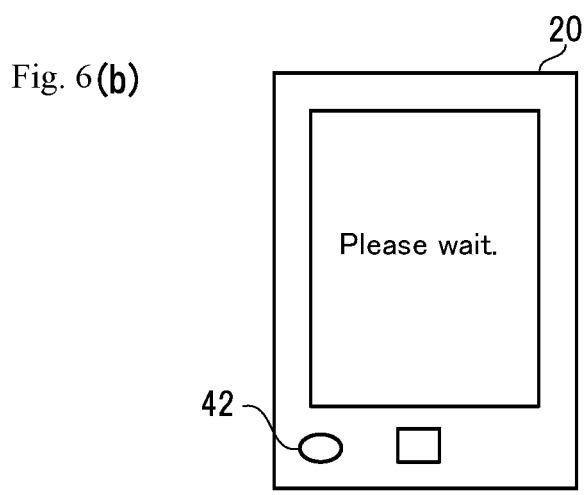
Figure 6C:
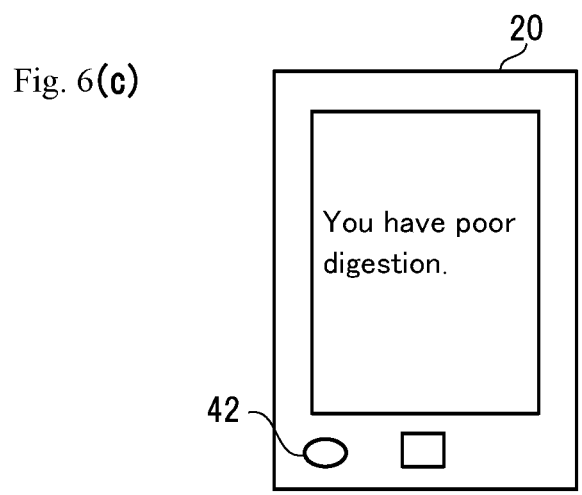

Next, the configurations of the server apparatus 10 and the terminal apparatus 20 according to the example embodiment will be more specifically described, using FIGS. 2 to 5. FIG. 2 is a block diagram more specifically showing the configurations of the server apparatus and the terminal apparatus according to the example embodiment of the invention. FIG. 3 is a diagram showing an external appearance of the terminal apparatus according to the example embodiment of the invention. FIG. 4 is a diagram showing an example of sensor data that is output by the odor sensor in the example embodiment of the invention. FIG. 5 is a diagram showing an example of a table that is used in selection of an analyzer and determination of preprocessing in the example embodiment of the invention. FIGS. 6(a) to 6(c) show an example of information that is displayed on the screen of the terminal apparatus.

First, the terminal apparatus 20 will be specifically described. As shown in FIG. 2, in the example embodiment, the terminal apparatus 20 further includes a program execution unit 25, a data reception unit 26, an environment information generation unit 27 and a data transmission unit 28, in addition to the sensor data collection unit 21, the analyzer acquisition unit 22, the analysis execution unit 23, and the analysis result holding unit 24.

The program execution unit 25 executes an application program that has been imported to the terminal apparatus 20. A program that performs processing according to odor sensor data analysis results obtained through odor sensor data sensed by the odor sensor 40 being analyzed by the terminal apparatus 20 and the server apparatus 10 is given as an example of an application program. Specifically, examples of an application program include a program that analyzes alcohol contained in the breath of a user of the terminal apparatus 20, a program that analyzes the body odor of a user of the terminal apparatus 20, and a program that analyzes the degree of ripeness of fruit from the odor of the fruit.

Also, in the example embodiment, the application program designates one or more odor analysis targets. Furthermore, the application program is also able to designate the accuracy at which to analyze the one or more odor analysis targets.

The data reception unit 26 receives the designation of the one or more odor analysis targets by the application program, and generates analysis condition information specifying the designated one or more odor analysis targets (specifically, information including a substance name, an identifier of the substance, etc.). Also, the data reception unit 26, when the accuracy at which to analyze the odor analysis target has been designated, furthermore, receives this designation, and generates analysis condition information specifying the odor analysis target and the accuracy.

Also, the data reception unit 26 includes a general-purpose application program interface (API). The data reception unit 26 is also able to receive designations other than from an application program described in the example embodiment, such as information on a designated odor from another apparatus via a network, for example. Information that the data reception unit 26 is capable of receiving may be information relating to alcohol or body odor, information on the contraction of a disease by an organism, information on the degree of ripeness of fruit, information on the degree of degradation of a structure or the like sought as an analysis result, other than the gas molecules constituting the actual odor. Based on this analysis target information, the data reception unit 26 specifies an appropriate analyzer from among analyzers registered in advance.

Also, in the case where the odor analysis target originates from a user, the data reception unit 26 is also able to, furthermore, receive input of personal information from the user, and create analysis condition information further specifying the received personal information. In this case, in the server apparatus 10, the analyzer selection unit 12 will select an analyzer with consideration for personal information.

The environment information generation unit 27 generates environment information, by specifying the environment around the odor sensor 40. Specifically, the terminal apparatus 20 internally includes an environmental sensor 41. The environment information generation unit 27 generates the environment information, by specifying the environment around the odor sensor 40 from sensor data output by the environmental sensor 41.

The data transmission unit 28 transmits the analysis condition information to the server apparatus 10. Also, the data transmission unit 28, when the environment information has been generated, adds the environment information to the analysis condition information, and transmits the analysis condition information to which the environment information is added to the server apparatus 10.

The environmental sensor 41 measures at least one of temperature and humidity around the odor sensor 40. A temperature sensor, a humidity sensor or a combination thereof are given as examples of the environmental sensor 41. In this case, the environment information specifies at least one of or both of temperature and humidity around the odor sensor 40. Also, in the abovementioned example, temperature and humidity are given as examples of the specified environment, but other examples include the concentration of atmospheric gas, illuminance and the amount of ultraviolet light. The environmental sensor 41 need only be a device that can measure the contents to be measured.

Also, in the example embodiment, the terminal apparatus 20 is constituted by a terminal apparatus (hereinafter, referred to as a "communication terminal") provided with a communication function such as a smartphone, and, furthermore, internally includes the odor sensor 40 and the environmental sensor 41. Also, as shown in FIG. 3, the terminal apparatus 20 includes a display device 29. Furthermore, a window 42 for guiding a gas targeted for measurement to the odor sensor 40 and a window 43 for the environmental sensor 41 are provided in the casing of the terminal apparatus 20. In FIG. 3, reference numeral 45 denotes an operation button of the terminal apparatus 20.

Also, in the example embodiment, the abovementioned MSS is used as the odor sensor 40, for example. In this case, the sensor data output by the odor sensor 40 will be as shown in FIG. 4. In the example in FIG. 4, sensor data output by one of the MSS elements constituting the MSS is shown. Also, the odor sensor 40 outputs sensor data at a set sampling rate. Note that i0, i1, i2 and so on that are shown in FIG. 4 are indexes, a description of which will be given later. Also, in the indexes, "i" indicates output from a specific MSS element. In the case of output from a different MSS element, a letter other than "i" is allocated.

Next, the server apparatus 10 will be specifically described. First, in the example embodiment, each analyzer that is being held by the analyzer holding unit 11 is an analysis model created in advance by machine learning. Analysis models are created by machine learning the features of sensor data, with a support vector machine, using sensor data output by the odor sensor 40 when there is a reaction to test odors as learning data, and using data specifying test odors as training data, for example.

Also, in the example embodiment, machine learning is performed utilizing the sparsity of sensor data, for example. In other words, the chemical behavior of an odor that serves as an analysis target and sensor elements and the physical characteristics of the odor sensor 40 are aggregated and appear in specific portions within the sensor data. In the example in FIG. 4, such behavior and characteristics appear in the rising portion of sensor data, the flat upper portion of the waveform, and the like. Accordingly, an appropriate analysis model can be built, even with machine learning that uses only a specific portion of the sensor data. Furthermore, the analysis accuracy can also be determined by the amount of data that is used in machine learning.

Thus, in the example embodiment, machine learning may be performed by extracting only an effective portion of sensor data serving as learning data. By using a technology called feature selection, for example, the portion effective for learning and analysis can be specified and extracted from sensor data serving as learning data. Also, the portion that is extracted at this time is specified by the indexes shown in FIG. 4, and the specified indexes are utilized in preprocessing in the terminal apparatus 20 discussed later.

The analyzer selection unit 12, in the example embodiment, acquires the analysis condition information transmitted thereto from the terminal apparatus 20. The analyzer selection unit 12 selects an analyzer capable of analyzing the odor analysis target, based on the acquired analysis condition information. Specifically, the analysis condition information includes the name of the odor analysis target, the accuracy at which to perform analysis, and the environment around the odor sensor 40, and thus the analyzer selection unit 12 selects an optimal analyzer with consideration for the contents thereof.

Also, the analyzer selection unit 12, in the example embodiment, upon selected an analyzer, specifies a feature amount to be extracted from sensor data, according to the selected analyzer. The feature amount that is specified corresponds to an effective portion of the sensor data utilized at the time of machine learning of that analyzer. The analyzer selection unit 12 then determines processing for extracting the specified feature amount as preprocessing, and selects a program module (hereinafter, referred to as a "feature amount extraction module") for executing the determined preprocessing to the terminal apparatus 20. In this case, the analyzer transmission unit 13 also transmits the feature amount extraction module to the terminal apparatus 20, in addition to the analyzer.

Specifically, the analyzer selection unit 12 performs selection of an analyzer and determination of corresponding preprocessing (feature amount extraction module), using the table shown in FIG. 5. In the example in FIG. 5, a corresponding feature amount extraction module, analysis target information, detection accuracy, compatible temperatures and an index list are registered for every analyzer on respective lines of the table. The analysis target information is information sought as an analysis result, with gas molecules constituting the actual odor that serves as an analysis target, breath alcohol concentration, the degree of ripeness of fruit and contraction of a specific disease being given as specific examples. Also, in this table, the index list on each line indicates sensor data used in learning by the corresponding analyzer, and indicates the feature amount that is extracted with the feature amount extraction module on the same line.

Here, functions of the analysis execution unit 23 and the analysis result holding unit 24 in the terminal apparatus 20 will be described more specifically. For example, assume that, in the example in FIG. 5, the server apparatus 10 select an analyzer 1, and transmits the analyzer 1 and a feature amount extraction module 1 to the terminal apparatus 20. In this case, in the terminal apparatus 20, the analysis execution unit 23, first, executes the feature amount extraction module 1 on the sensor data collected by the sensor data collection unit 21, and, as preprocessing, extracts data corresponding to i0, . . . i99 in the index list from the sensor data as a feature amount.

In this way, in the example embodiment, since thinning of sensor data is performed by preprocessing, the load on the transmission apparatus 20 is eased. Also, analysis of an odor becomes possible, because thinning of sensor data is performed in conformance with an analyzer corresponding to the odor analysis target.

Also, the analysis execution unit 23 executes analysis processing, by applying an analyzer to the sensor data that has undergone preprocessing, that is, the extracted feature amount. Specifically, the analysis execution unit 23 analyzes the odor analysis target, using an analyzer.

Furthermore, the analysis execution unit 23 is also able to estimate the level of the analyzed odor analysis target from the result of the analysis processing. Specifically, the analysis execution unit 23 estimates the graded level of an odor, according to the concentration of odor analysis target. Also, in this case, the analysis execution unit 23 passes information indicating the estimated level of the odor to the analysis result holding unit 24, as information indicating the result of the analysis processing.

In the terminal apparatus 20, the analysis result holding unit 24 is thereby able to display the estimated level of the odor on the screen of the display device 29. Also, in the example embodiment, the analysis result holding unit 24 is able to display information supporting operations by the user on the screen of the display device 29, as shown in FIGS. 6(a) to 6(c).

[Apparatus Operations]

Next, operations of the server apparatus 10 and the terminal apparatus 20 according to the example embodiment will be described using FIGS. 7 and 8. Also, in the following description, FIGS. 1 to 6 will be referred to as appropriate. Furthermore, in the example embodiment, the odor sensor data analysis method is implemented, by operating the server apparatus 10 and the terminal apparatus 20. Therefore, the following description of the operations of the server apparatus 10 and the terminal apparatus 20 will be given in place of a description of the odor sensor data analysis method according to the example embodiment.

Figure 7:
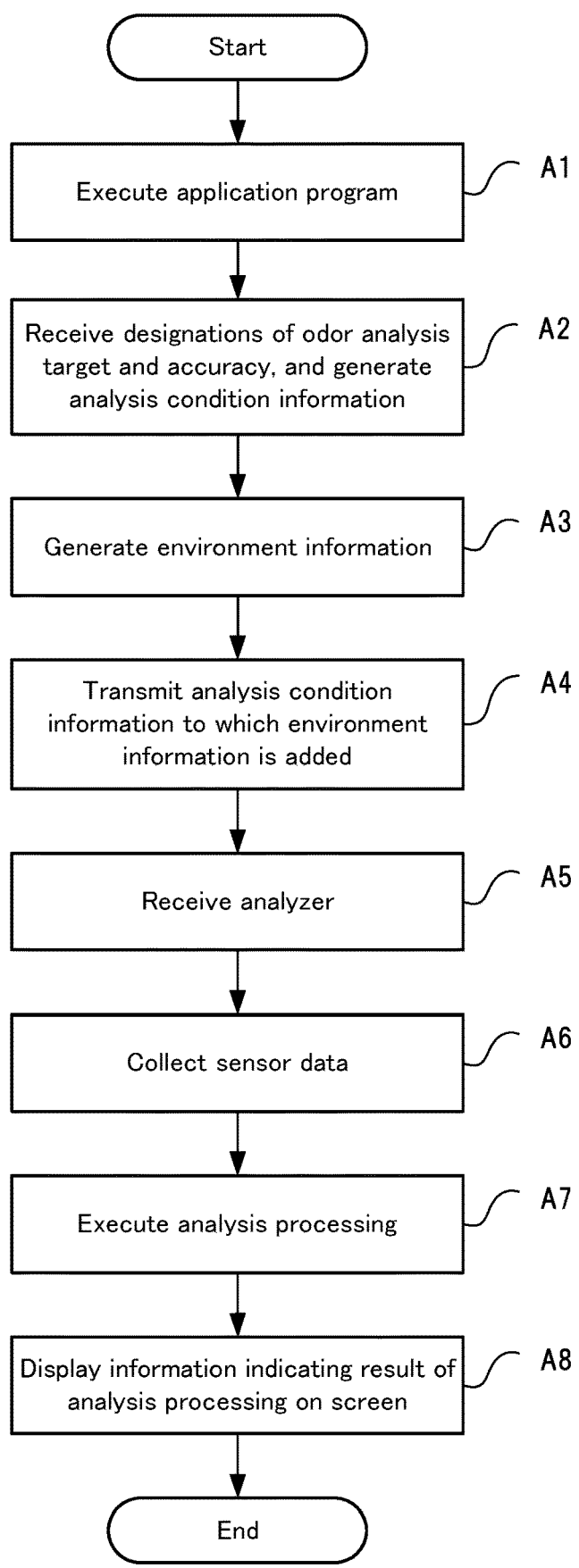
FIG. 7 is a flowchart showing operations of the terminal apparatus according to the example embodiment of the invention.

First, operations of the terminal apparatus 20 will be specifically described using FIG. 7. FIG. 7 is a flowchart showing operations of the terminal apparatus according to the example embodiment of the invention.

Initially, as shown in FIG. 7, in the terminal apparatus 20, the program execution unit 25 executes the application program (step A1).

Next, when the application program designates one or more odor analysis targets and the accuracy at which to perform analysis, the data reception unit 26 receives these designations and generates analysis condition information (step A2).

Next, the environment information generation unit 27 generates environment information, by specifying the environment around the odor sensor 40, from the sensor data output by the environmental sensor 41 (step A3).

Next, the data transmission unit 28 adds the environment information generated in step A3 to the analysis condition information generated in step A2, and transmits the analysis condition information to which the environment information is added to the server apparatus 10 (step A4).

Upon step A4 being executed, in the server apparatus 10, steps B1 to B4 shown in FIG. 8 described later are executed. In the terminal apparatus 20, the analyzer acquisition unit 22 thereby receives an analyzer from the server apparatus 10, and acquires this analyzer (step A5). In step A5, the analyzer acquisition unit 22, furthermore, also receives a feature amount extraction module transmitted thereto from the server apparatus 10, and also acquires this feature amount extraction module.

Next, the sensor data collection unit 21 collects the sensor data that is output by the odor sensor 40 (step A6).

Next, the analysis execution unit 23 executes preprocessing on the sensor data collected in step A6, using the feature amount extraction module, and executes analysis processing on the designated odor analysis target, by applying the analyzer selected in step A6 to the preprocessed sensor data (step A7). Also, the analysis execution unit 23 passes information indicating the result of the analysis processing to the analysis result holding unit.

Next, the analysis result holding unit 24 receives the information indicating the result of the analysis processing in step A7, and displays the received information on the screen of the display device 29 (step A8).

Figure 8:
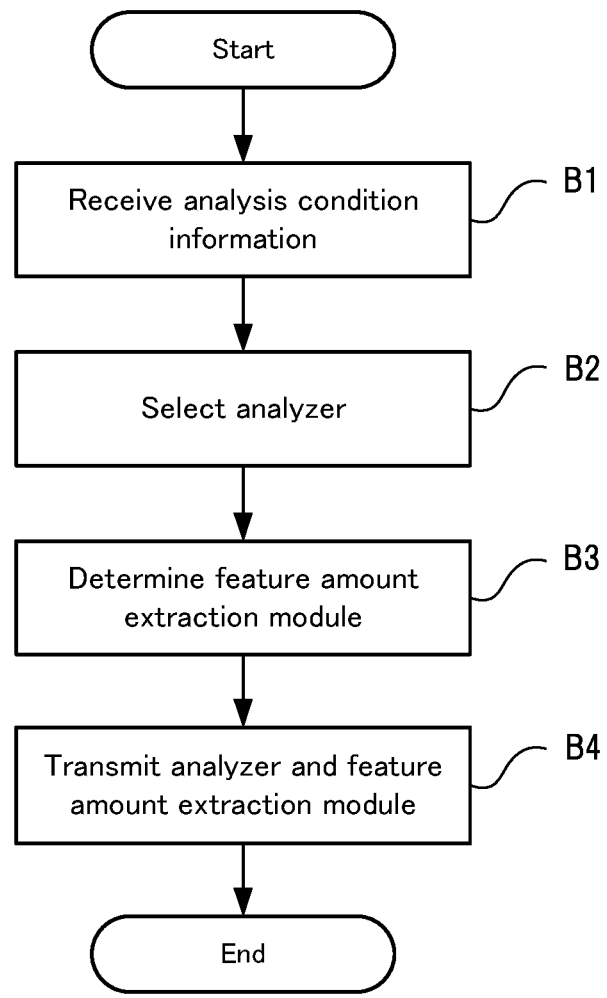
FIG. 8 is a flowchart showing operations of the server apparatus according to the example embodiment of the invention.

Next, operations of the server apparatus 10 will be specifically described using FIG. 8. FIG. 8 is a flowchart showing operations of the server apparatus according to the example embodiment of the invention.

Upon steps A1 to A4 shown in FIG. 7 being executed, the server apparatus 10, as shown in FIG. 8, receives the analysis condition information transmitted in step A4 (step B1).

Next, the analyzer selection unit 12 selects an analyzer capable of analyzing the designated odor analysis target, from among the analyzers that are being held in the analyzer holding unit 11, based on the analysis condition information (step B2).

Next, the analyzer selection unit 12 determines a feature amount extraction module corresponding to the analyzer selected in step B2 (step B3). Thereafter, the analyzer transmission unit 13 transmits the analyzer selected in step B2 and the feature amount extraction module determined in step B3 to the terminal apparatus 20 (step B4). After execution of step B4, in the terminal apparatus 20, steps A5 to A8 are executed.

Specifically, in steps B2 to B4, the analyzer selection unit 12, first, collates the designated odor analysis target with the analysis target information and selects matching lines from the table shown in FIG. 5. Next, the analyzer selection unit 12 specifies lines in which the compatible temperatures match the temperature that is specified by the environment information and the detection accuracy matches the designated accuracy, from among the selected lines. Furthermore, the analyzer selection unit 12 specifies a line in which the size of the index list is smallest, from among the specified lines. The analyzer selection unit 12 then selects an analyzer and a feature amount extraction module that correspond to this line that was specified last, and transmits the selected analyzer and feature amount extraction module to the terminal apparatus 20.

[Effect of Example Embodiment]

As described above, according to the example embodiment, in the server apparatus 10, the appropriate analyzer and feature amount extraction module are selected with consideration for the environment, and analysis of the odor analysis target is performed, by the selected analyzer and feature amount extraction module being implemented in the terminal apparatus 20. Thus, the terminal apparatus 20 does not need to implement a large number of analyzers in advance. According to the example embodiment, it becomes possible to utilize an analyzer adapted to the situation, without implementing a large number of analyzers, in the case of analyzing odors using an odor sensor whose analysis target is not fixed.

[Variations]

Figure 9:
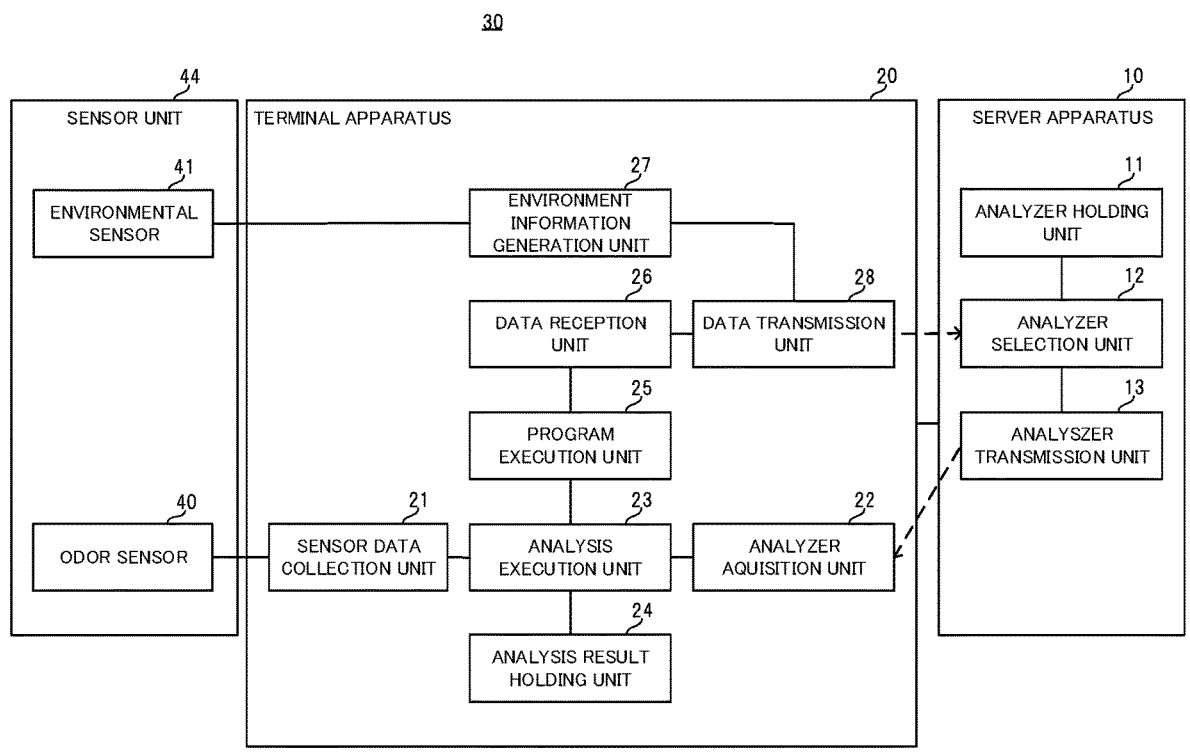
FIG. 9 is a block diagram showing configurations of the server apparatus and a variation of the terminal apparatus according to the example embodiment of the invention.
Figure 10:
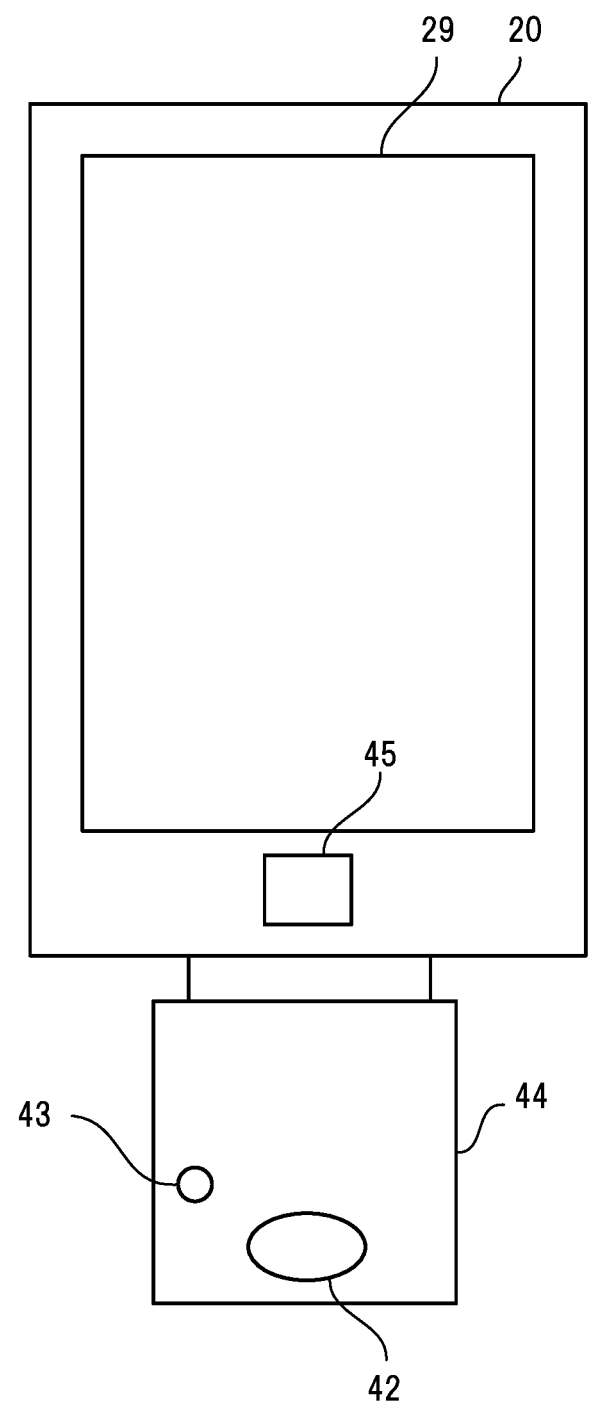
FIG. 10 is a diagram showing an external appearance of the variation of the terminal apparatus according to the example embodiment of the invention.

In the example shown in FIGS. 1 and 2, the terminal apparatus 20 is constituted by a communication terminal, and internally includes the odor sensor 40 and the environmental sensor 41, although, in the example embodiment, the terminal apparatus 20 is not limited to this configuration. Here, a variation of the terminal apparatus 20 according to the example embodiment will be described, using FIGS. 9 and 10. FIG. 9 is a block diagram showing configurations of the server apparatus and the variation of the terminal apparatus according to the example embodiment of the invention. FIG. 10 is a diagram showing an external appearance of the variation of the terminal apparatus according to the example embodiment of the invention.

As shown in FIG. 9, in this variation, the odor sensor 40 and the environmental sensor 41 are provided outside the terminal apparatus 20. Specifically, the odor sensor 40 and the environmental sensor 41 are housed in one casing, and constitute a sensor unit 44. Also, as shown in FIG. 10, the sensor unit 44 is connected to the terminal apparatus 20, via an interface for external connection of the terminal apparatus 20, which is a communication terminal.

According to this variation, detection of substances in the atmosphere can be executed, by connecting the sensor unit 44 to a general-purpose communication terminal 20. Also, the sensor unit 44 is directly connected to the terminal apparatus 20 in this variation, but the connection therebetween need only be implemented in a manner that enables communication, and may be implemented wirelessly or by cable.

APPLICATION EXAMPLE 1

The example embodiment can, for example, be applied in the case of estimating the freshness of perishable foods, in a retail store that sells perishable foods. In this example, the odor of perishable foods is given as the odor analysis target.

Specifically, assume that a sales person has started up an application program for estimating the freshness of perishable foods in the terminal apparatus 20, and selected a perishable food to serve as an estimation target on the application program. In this case, the application program designates the selected perishable food and the accuracy at which to perform analysis. The data reception unit 26 thereby receives these designations and generates analysis condition information specifying the received perishable food and accuracy.

Also, in the terminal apparatus 20, the environment information generation unit 27 generates environment information based on sensor data from the environmental sensor 41. Thereafter, the data transmission unit 28 adds the environment information to the analysis condition information, and transmits the analysis condition information to which the environment information is added to the server apparatus 10. The server apparatus 10 then selects an optimal analyzer and feature amount extraction module, and transmits the selected analyzer and module to the terminal apparatus 20.

In the terminal apparatus 20, the analysis execution unit 23 executes preprocessing using the feature amount extraction module transmitted thereto, and, furthermore, analyzes the odor of the selected perishable food, using the analyzer transmitted thereto. The analysis execution unit 23 then estimates the deterioration of the perishable food, based on the result of the analysis processing. Specifically, the analysis execution unit 23 estimates which of graded assessments set in advance, such as "unripe", "optimally ripe", "overripe-ish" and "spoiled", for example, is applicable.

The analysis result holding unit 24 is able to display the graded assessment that is estimated on the screen of the display device 29. The analysis result holding unit is also able to display a message to the user on the screen at the same time, in addition to the graded assessment. Specifically, the analysis result holding unit 24 displays, as messages, for example, "markdown not necessary yet" in the case where the graded assessment is "unripe", "mark as good for eating" in the case of "optimally ripe", "mark down now" in the case of "overripe-ish", and "discard" in the case of "spoiled".

If the terminal apparatus 20 is provided with a function of setting a price according to the graded assessment in the case where information indicating a specific price that depends on the graded assessment is transmitted thereto from the server apparatus 10, the analysis result holding unit is also able to display a price corresponding to the graded assessment on the screen. Furthermore, the terminal apparatus 20, in the case of being provided with a function of printing and attaching price tag labels, prints and attaches a price tag label of the price when a price is displayed on the screen.

Also, in the case where the terminal apparatus 20 is used by a buyer in the retail store, the analysis result holding unit 24 is also able to display a discount price that depends on the graded assessment on the screen, in addition to the graded assessment. Note that, in this case, it is assumed that the terminal apparatus 20 receives data on the discount price that depends on the graded assessment from a server apparatus or the like of the retail store, at the point in time that the buyer is in the retail store. In the case where such a mode is assumed, the sales person in the retail store does not need to change the price tag labels every fixed period, and time and effort for the sales person is reduced.

APPLICATION EXAMPLE 2

Also, the example embodiment can, for example, be applied to the healthcare of users. In this example, a person's expiration is given as the odor analysis target.

Specifically, assume that a user has started up an application program for estimating state of health from expiration in the terminal apparatus 20, and input his or her own information. The following are given as information that is input by the user.

Attribute data: date of birth, area of residence, gender, occupation, height, weight, etc.

Daily routine data: bowel movement, menstrual cycle, dietary composition, drinking habits, etc.

Targets: Target weight (for diet purposes), improved numbers

In this case, the data reception unit 26 also receives the input information, in addition to expiration, which is the odor analysis target, and accuracy, and generates analysis condition information specifying this received information. Upon the data transmission unit 28 transmitting the analysis condition information to the server apparatus 10, the server apparatus 10, in the application example 2, selects an optimal analyzer and feature amount extraction module, with use also of the information input by the user, and transmits the selected analyzer and module to the terminal apparatus 20.

In the terminal apparatus 20, the analysis execution unit 23 executes preprocessing using the feature amount extraction module transmitted thereto, and, furthermore, analyzes the expiration of the user, using the analyzer transmitted thereto. The analysis execution unit 23 then estimates the state of health of the user by graded assessment, based on the result of the analysis processing.

Also, in the case where the application program is geared toward the diet of the user, the analysis execution unit 23 may estimate the degree of progress of the diet, or estimate the effectiveness of actual diets (dietary restrictions, ingestion of certain types of medication, etc.).

Also, the result of estimation by the analysis execution unit 23 may be recorded together with the time of estimation by the server apparatus 10 or by a different server apparatus. In this case, the server apparatus is able to estimate how the state of health of the user will change, based on the history of the estimation results of the user, and is able to display the estimation results on the screen of the terminal apparatus 20. For example, in the case where the state of health is transitioning in a positive direction, displaying this fact on the screen can help to motivate the user. In the case where the state of health is transitioning in a negative direction, the server apparatus is also able to alert the user by also displaying this fact on the screen.

The server apparatus is also able to determine, from the history of accumulated estimation results, whether or not the user is achieving his or her ultimate goal, how much longer the goal will take to achieve, or how long the goal took to achieve. Furthermore, the server apparatus, by machine learning the degree of goal achievement by respective users and the path taken to get there, is also able to present the period taken for other users to achieve their goals, the probability of achieving the goal, actions required to achieve the goal, and the like

[Program 1]

A first program according to the example embodiment need only be a program that causes a computer to execute steps A1 to A8 shown in FIG. 7. The terminal apparatus 20 according to the example embodiment can be realized, by installing this program on a computer and executing the installed program. In this case, a processor of the computer performs processing while functioning as the sensor data collection unit 21, the analyzer acquisition unit 22, the analysis execution unit 23, the analysis result holding unit 24, the program execution unit 25, the data reception unit 26, the environment information generation unit 27, and the data transmission unit 28. Also, a computer mounted in a communication terminal and a general-purpose computer are given as examples of the computer.

Also, the first program according to the example embodiment may be executed by a computer system built from a plurality of computers. In this case, for example, the computers may respectively function as one of the sensor data collection unit 21, the analyzer acquisition unit 22, the analysis execution unit 23, the analysis result holding unit 24, the program execution unit 25, the data reception unit 26, the environment information generation unit 27, and the data transmission unit 28.

[Program 2]

A second program according to the example embodiment need only be a program that causes a computer to execute steps B1 to B4 shown in FIG. 8. The server apparatus 10 according to the example embodiment can be realized, by installing this program on a computer and executing the installed program. In this case, a processor of the computer performs processing while functioning as the analyzer holding unit 11, the analyzer selection unit 12 and the analyzer transmission unit 13. Also, a general-purpose computer and a server computer are given as examples of the computer.

The second program according to the example embodiment may also be executed by a computer system built from a plurality of computers. In this case, for example, the computers may respectively function as one of the analyzer holding unit 11, the analyzer selection unit 12, and the analyzer transmission unit 13.

[Physical Configuration]

Figure 11:
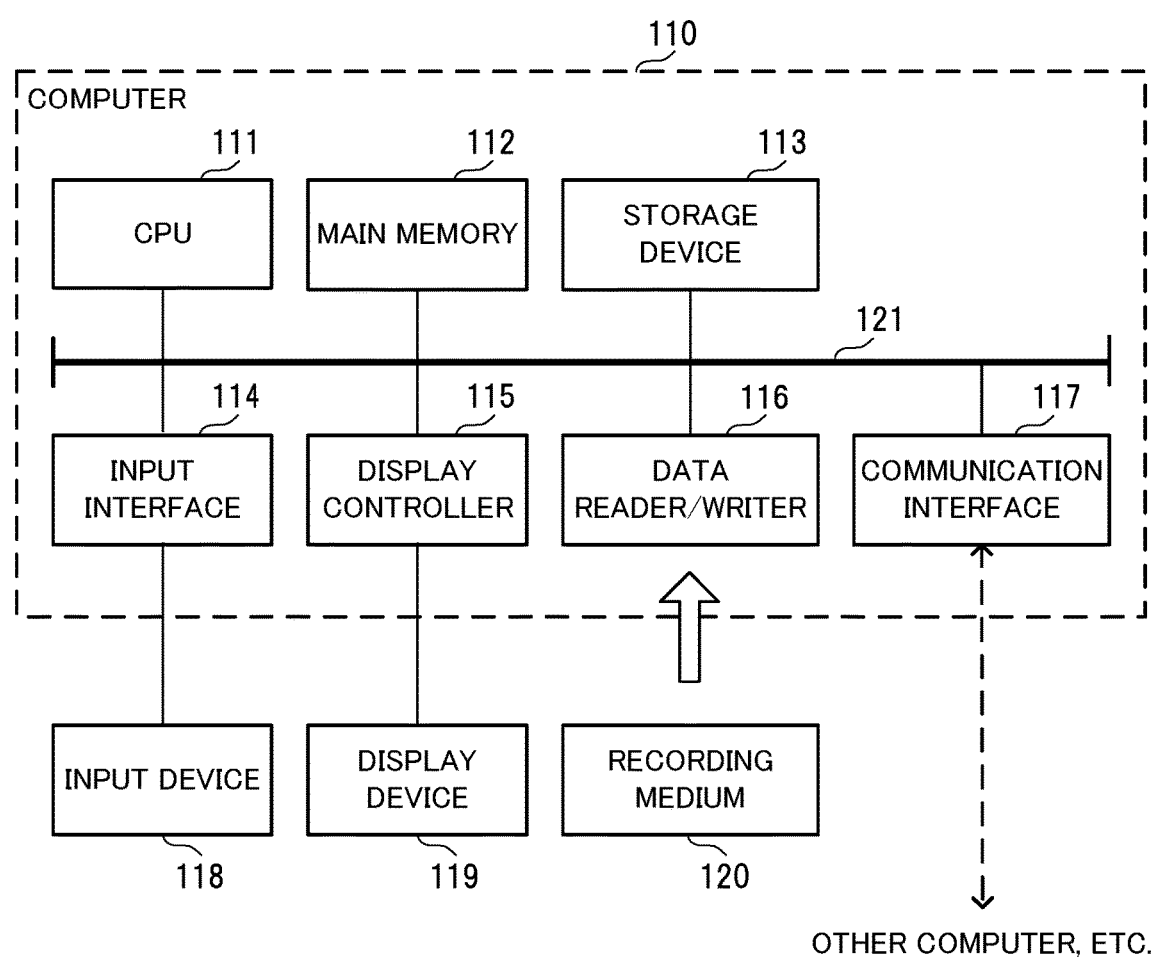
FIG. 11 is a block diagram showing an example of a computer that realizes the terminal apparatus and the server apparatus according to the example embodiment of the invention.

Here, an example of a computer capable of executing the first program or the second program according to the example embodiment will be described using FIG. 11. FIG. 11 is a block diagram showing an example of a computer that realizes the terminal apparatus and the server apparatus according to the example embodiment of the invention.

As shown in FIG. 11, a computer 110 includes a CPU (Central Processing Unit) 111, a main memory 112, a storage device 113, an input interface 114, a display controller 115, a data reader/writer 116, and a communication interface 117. These units are connected in a manner that enables data communication, via a bus 121.

The CPU 111 implements various computational operations, by extracting programs (code) according to the example embodiment stored in the storage device 113 to the main memory 112, and executing these programs in predetermined order. The main memory 112, typically, is a volatile storage device such as a DRAM (Dynamic Random Access Memory). Also, programs according to the example embodiment are provided in a state of being stored on a computer-readable recording medium 120. Note that programs according to the example embodiment may be distributed over the Internet connected via the communication interface 117. Note also that the computer 110 may include a GPU (Graphics Processing Unit) or an FPGA (Field-Programmable Gate Array), in addition to the CPU 111 or instead of the CPU 111.

Also, a semiconductor storage device such as a flash memory is given as a specific example of the storage device 113, other than a hard disk drive. The input interface 114 mediates data transmission between the CPU 111 and input devices 118 such as a keyboard and a mouse. The display controller 115 is connected to a display device 119 and controls display by the display device 119.

The data reader/writer 116 mediates data transmission between the CPU 111 and the recording medium 120, and executes readout of programs from the recording medium 120 and writing of processing results of the computer 110 to the recording medium 120. The communication interface 117 mediates data transmission between the CPU 111 and other computers.

Also, a general-purpose semiconductor storage device such as a CF (Compact Flash (registered trademark)) card or an SD (Secure Digital) card, a magnetic recording medium such as a flexible disk, and an optical recording medium such as a CD-ROM (Compact Disk Read Only Memory) are given as specific examples of the recording medium 120.

Note that the server apparatus 10 and the terminal apparatus 20 according to the example embodiment are also respectively realizable by using hardware corresponding to the respective units, rather than by a computer on which programs are installed. Furthermore, the server apparatus 10 and the terminal apparatus 20 may respectively be realized in part by programs, and the remaining portion may be realized by hardware.

The example embodiment described above can be partially or wholly realized by supplementary notes 1 to 27 described below, but the invention is not limited to the following description.

(Supplementary Note 1)

A server apparatus server apparatus configured to be communicably connected to a terminal apparatus for collecting sensor data from an odor sensor that outputs the sensor data in reaction to a plurality of types of odors and performing analysis of an odor analysis target, the server apparatus comprising:

an analyzer holding unit configured to hold a plurality of analyzers for analyzing specific odor analysis targets by analyzing the sensor data;

an analyzer selection unit configured to select an analyzer capable of analyzing a designated odor analysis target, from among the plurality of analyzers; and an analyzer transmission unit configured to transmit the selected analyzer to the terminal apparatus.

(Supplementary Note 2)

The server apparatus according to supplementary note 1, in which analysis condition information specifying the odor analysis target is transmitted from the terminal apparatus to the server apparatus, and the analyzer selection unit selects the analyzer, based on the analysis condition information.

(Supplementary Note 3)

The server apparatus according to supplementary note 1 or 2, in which the analysis condition information further includes accuracy information specifying an accuracy at which to perform analysis and environment information specifying an environment around the odor sensor.

(Supplementary Note 4)

The server apparatus according to supplementary note 3, in which the environment information specifies at least one of or both of temperature and humidity around the odor sensor, as the environment around the odor sensor.

(Supplementary Note 5)

The server apparatus according to any of supplementary notes 2 to 4, in which, in a case where the odor analysis target originates from a user, the analysis condition information includes personal information of the user.

(Supplementary Note 6)

The server apparatus according to any of supplementary notes 1 to 5, in which one or more odor analysis targets are designated by an application program that is executed in the terminal apparatus, and analysis condition information specifying the designated one or more odor analysis targets is transmitted from the terminal apparatus to the server apparatus.

(Supplementary Note 7)

A terminal apparatus for collecting sensor data from an odor sensor that outputs the sensor data in reaction to a plurality of types of odors and performing analysis of an odor analysis target to carry out:

a sensor data collection unit configured to collect the sensor data;

an analyzer acquisition unit configured to, in a case where an analyzer capable of analyzing a designated odor analysis target is transmitted to the terminal apparatus from a server apparatus that holds a plurality of analyzers for analyzing specific odor analysis targets by analyzing the sensor data, acquire the analyzer transmitted thereto;

an analysis execution unit configured to execute analysis processing of the designated odor analysis target, by applying the acquired analyzer to the collected sensor data; and an analysis result holding unit configured to hold information indicating a result of the analysis processing.

(Supplementary Note 8)

The terminal apparatus according to supplementary note 7, further including:

a data reception unit configured to receive a designation of one or more odor analysis targets, and generate analysis condition information specifying one or more substances that serve as the designated one or more analysis targets; and a data transmission unit configured to transmit the generated analysis condition information to the server apparatus.

(Supplementary Note 9)

The terminal apparatus according to supplementary note 8, further including:

an environment information generation unit configured to generate environment information specifying an environment around the odor sensor, in which the data reception unit is configured to receive a designation of an accuracy at which to perform analysis, and generates analysis condition information further specifying the designated accuracy at which to perform analysis, and the data transmission unit is configured to add the environment information to the analysis condition information, and transmit the analysis condition information to which the environment information is added to the server apparatus.

(Supplementary Note 10)

The terminal apparatus according to supplementary note 9, in which the environment information generation unit is configured to generate environment information specifying at least one of or both of temperature and humidity, from sensor data output by a sensor that measures at least one of temperature and humidity around the odor sensor.

(Supplementary Note 11)

The terminal apparatus according to any of supplementary notes 8 to 10, in which, in a case where the odor analysis target originates from a user, the data reception unit is configured to receive input of personal information of the user, and creates analysis condition information further specifying the received personal information.

(Supplementary Note 12)

The terminal apparatus according to supplementary note 8, further including:

a program execution unit configured to execute an application program, in which the data reception unit is configured to, when a designation of one or more odor analysis targets by the application program is received, generate analysis condition information specifying the designated one or more odor analysis targets.

(Supplementary Note 13)

The terminal apparatus according to any of supplementary notes 7 to 12, in which the analysis execution unit is configured to estimate a level of the odor analysis target from the result of the analysis processing, and the analysis result holding unit is configured to display the estimated level on a screen, as the information indicating the result of the analysis processing.

(Supplementary Note 14)

An odor sensor data analysis method that uses a terminal apparatus for collecting sensor data from an odor sensor that outputs the sensor data in reaction to a plurality of types of atmospheric substances and performing analysis of an odor analysis target and a server apparatus configured to be communicably connected to the terminal apparatus, the method comprising:

(a) a step of, with the terminal apparatus, collecting the sensor data;

(b) a step of, with the server apparatus, selecting an analyzer capable of analyzing a designated odor analysis target, from among a plurality of analyzers for analyzing specific odor analysis targets by analyzing the sensor data;

(c) a step of, with the server apparatus, transmitting the selected analyzer to the terminal apparatus;

(d) a step of, with the terminal apparatus, acquiring the analyzer transmitted thereto from the server apparatus;

(e) a step of, with the terminal apparatus, executing analysis processing of the designated odor analysis target, by applying the acquired analyzer to the collected sensor data; and (f) a step of, with the terminal apparatus, holding information indicating a result of the analysis processing.

(Supplementary Note 15)

A computer-readable recording medium that includes a program recorded thereon, the program including instructions that cause a computer configured to be communicably connected to a terminal apparatus for collecting sensor data from an odor sensor that outputs the sensor data in reaction to a plurality of types of atmospheric substances and performing analysis of an odor analysis target to carry out:

(a) a step of holding a plurality of analyzers for analyzing specific odor analysis targets by analyzing the sensor data;

(b) a step of selecting an analyzer capable of analyzing a designated odor analysis target, from among the plurality of analyzers; and (c) a step of transmitting the selected analyzer to the terminal apparatus.

(Supplementary Note 16)

The computer-readable recording medium according to supplementary note 15, in which analysis condition information specifying an odor analysis target is transmitted from the terminal apparatus to the server device, and in the (b) step, the analyzer is selected, based on the analysis condition information.

(Supplementary Note 17)

The computer-readable recording medium according to supplementary note 16, in which the analysis condition information further includes accuracy information specifying an accuracy at which to perform analysis and environment information specifying an environment around the odor sensor.

(Supplementary Note 18)

The computer-readable recording medium according to supplementary note 17, in which the environment information specifies at least one of or both of temperature and humidity around the odor sensor, as the environment around the odor sensor.

(Supplementary Note 19)

The computer-readable recording medium according to any of supplementary notes 16 to 18, in which, in a case where the odor analysis target originates from a user, the analysis condition information includes personal information of the user.

(Supplementary Note 20)

The computer-readable recording medium according to any of supplementary notes 15 to 19, in which one or more odor analysis targets are designated by an application program that is executed in the terminal apparatus, and analysis condition information specifying the designated one or more odor analysis targets is transmitted from the terminal apparatus to the server apparatus.

(Supplementary Note 21)

A computer-readable recording medium that includes a program recorded thereon, the program including instructions that cause a computer for collecting sensor data from an odor sensor that outputs the sensor data in reaction to a plurality of types of odors and performing analysis of an odor analysis multi-design to carry out:

(a) a step of collecting the sensor data;

(b) a step of, in a case where an analyzer capable of analyzing a designated odor analysis target is transmitted to the terminal apparatus from a server apparatus that holds a plurality of analyzers for analyzing specific odor analysis targets by analyzing the sensor data, acquiring the analyzer transmitted thereto;

(c) a step of executing analysis processing of the designated odor analysis target, by applying the acquired analyzer to the collected sensor data; and (d) a step of holding information indicating a result of the analysis processing.

(Supplementary Note 22)

The computer-readable recording medium according to supplementary note 21, in which the program further includes instructions that cause the computer to carry out:

(e) a step of receiving a designation of one or more odor analysis targets, and generating analysis condition information specifying one or more substance that serves as the designated one or more analysis targets; and (f) a step of transmitting the generated analysis condition information to the server apparatus.

(Supplementary Note 23)

The computer-readable recording medium according to supplementary note 22, in which the program further includes instructions that cause the computer to carry out:

(g) a step of generating environment information specifying an environment around the odor sensor, in the (e) step, a designation of an accuracy at which to perform analysis is received, and analysis condition information further specifying the designated accuracy at which to perform analysis is generated, and in the (f) step, the environment information is added to the analysis condition information, and the analysis condition information to which the environment information is added is transmitted to the server apparatus.

(Supplementary Note 24)

The computer-readable recording medium according to supplementary note 23, in which, in the (g) step, environment information specifying at least one of or both of temperature and humidity is generated, from sensor data output by a sensor that measures at least one of temperature and humidity around the odor sensor.

(Supplementary Note 25)

The computer-readable recording medium according to any of supplementary notes 22 to 24, in which, in the (e) step, in the case where the odor analysis target originates from a user, input of personal information of the user is received, and analysis condition information further specifying the received personal information is created.

(Supplementary Note 26)

The computer-readable recording medium according to supplementary note 22, in which the program further includes instructions that cause the computer to carry out:

(h) a step of executing an application program, and in the (e) step, when a designation of one or more odor analysis targets by the application program is received, analysis condition information specifying the designated one or more odor analysis targets is generated.

(Supplementary Note 27)

The computer-readable recording medium according to any of supplementary notes 21 to 26, in which, in the (c) step, a level of the odor analysis target is estimated from the result of the analysis processing, and in the (d) step, information indicating the estimated level is displayed on a screen, as the information indicating the result of the analysis processing.

Although the invention of the present application has been described above with reference to an example embodiment, the invention is not limited to the example embodiment described above. Various modifications apparent to those skilled in the art can be made to the configurations and details of the invention within the scope of the invention.

INDUSTRIAL APPLICABILITY

As described above, according to the invention, it becomes possible to utilize an analyzer adapted to the situation, without implementing a large number of analyzers, in the case of executing substance detection using an odor sensor whose analysis target is not fixed. The invention is useful in various fields in which odor sensors are utilized.

LIST OF REFERENCE SIGNS

10 Server apparatus
11 Analyzer holding unit
12 Analyzer selection unit
13 Analyzer transmission unit
20 Terminal apparatus
21 Sensor data collection unit
22 Analyzer acquisition unit
23 Analysis execution unit
24 Analysis result holding unit
25 Program execution unit
26 Data reception unit
27 Environment information generation unit
28 Data transmission unit
29 Display device
30 System
40 Odor sensor
41 Environmental sensor
42 Window
43 Window
44 Sensor unit
45 Operation button
110 Computer
111 CPU
112 Main memory
113 Storage device
114 Input interface
115 Display controller
116 Data reader/writer
117 Communication interface
118 Input device
119 Display device
120 Recording medium
121 Bus

The invention claimed is:

1. An odor analyzing system including a terminal apparatus and a server the terminal, wherein the server apparatus comprises:
  a processor configured to:
    select an analyzer to analyze a designated odor analysis target, from among a plurality of analyzers configured to analyze specific odor analysis targets by analyzing sensor data, based on analysis condition information indicating condition of analysis accuracy for analyzing the designated odor analysis target and condition of environment around an odor sensor,
    wherein the analyzer is an analysis model created in advance by machine learning; and
    transmit the selected analyzer to the terminal apparatus, and
  the terminal apparatus configured to:
    collect the sensor data from the odor sensor that outputs the sensor data in reaction to a plurality of types of odors,
    acquire the selected analyzer from the server apparatus, analyze the designated odor analysis target by applying the selected analyzer to collected sensor data, and
    output a result of analyzing to display device.

2. The server apparatus according to claim 1,
wherein the environment information specifies at least one of or both of temperature and humidity around the odor sensor, as the environment around the odor sensor.

3. The server apparatus according to claim 1,
wherein, in a case where the odor analysis target originates from a user, the analysis condition information includes personal information of the user.

4. The server apparatus according to claim 1,
wherein one or more odor analysis targets are designated by an application program that is executed in the terminal apparatus, and analysis condition information specifying the designated one or more odor analysis targets is transmitted from the terminal apparatus to the server apparatus.

5. An odor sensor data analysis method that uses a terminal apparatus for collecting sensor data from an odor sensor that outputs the sensor data in reaction to a plurality of types of atmospheric substances and performing analysis of an odor analysis target and a server apparatus configured to be communicably connected to the terminal apparatus, the method comprising:

collecting, by the terminal apparatus, the sensor data;

selecting, by the server apparatus, an analyzer to analyze a designated odor analysis target, from among a plurality of analyzers configured to analyze specific odor analysis targets by analyzing sensor data, based on analysis condition information indicating condition of analysis accuracy for analyzing the designated odor analysis target and condition of environment around an odor sensor, wherein the analyzer is an analysis model created in advance by machine learning;

transmitting, by the server apparatus, the selected analyzer to the terminal apparatus;

acquiring, by the terminal apparatus, the analyzer transmitted thereto from the server apparatus;

executing, by the terminal apparatus, analysis processing of the designated odor analysis target, by applying the acquired analyzer to the collected sensor data; and outputting, by the terminal apparatus, a result of analyzing to display device.

6. A non-transitory computer-readable recording medium having stored thereon a program including instructions, which when executed by a computer performs a method comprising:

holding a plurality of analyzers for analyzing specific odor analysis targets by analyzing sensor data;

selecting an analyzer to analyze a designated odor analysis target, from among the plurality of analyzers, based on analysis condition information indicating condition of analysis accuracy for analyzing the designated odor analysis target and condition of environment around an odor sensor, wherein the analyzer is an analysis model created in advance by machine learning; and transmitting the selected analyzer to a terminal apparatus, which collects the sensor data from the odor sensor that outputs the sensor data in reaction to a plurality of types of atmospheric substances and performs analysis of the designated odor analysis target.

7. The non-transitory computer-readable recording medium according to claim 6, wherein the environment information specifies at least one of or both of temperature and humidity around the odor sensor, as the environment around the odor sensor.

8. The non-transitory computer-readable recording medium according to claim 6, wherein, in a case where the odor analysis target originates from a user, the analysis condition information includes personal information of the user.

9. The non-transitory computer-readable recording medium according to claim 6, wherein one or more odor analysis targets are designated by an application program that is executed in the terminal apparatus, and analysis condition information specifying the designated one or more odor analysis targets is transmitted from the terminal apparatus to the computer.

10. A non-transitory computer-readable recording medium having stored thereon, a program including instructions, which when executed by a computer performs a method for performing analysis of an odor analysis multidesign, the method comprising:

collecting sensor data from an odor sensor that outputs the sensor data in reaction to a plurality of types of odors;

acquire an analyzer to analyze a designated odor analysis target form a sever apparatus, the analyze selected from among the plurality of analyzers, based on analysis condition information indicating condition of analysis accuracy for analyzing the designated odor analysis target and condition of environment around the odor sensor, wherein the analyzer is an analysis model created in advance by machine learning;

executing analysis processing of the designated odor analysis target, by applying the analyzer to the collected sensor data; and outputting, by the terminal apparatus, a result of analyzing to display device.

11. The non-transitory computer-readable recording medium according to claim 10, wherein the program further includes instructions that cause the computer to perform the method further comprising:

receiving a designation of one or more odor analysis targets, and generating analysis condition information specifying one or more substances that serve as the designated one or more analysis targets; and transmitting the generated analysis condition information to the server apparatus.

12. The non-transitory computer-readable recording medium according to claim 11, wherein the program further includes instructions that cause the computer to perform the method further comprising:

generating environment information specifying an environment around the odor sensor, a designation of an accuracy at which to perform analysis is received, and analysis condition information further specifying the designated accuracy at which to perform analysis is generated, and the environment information is added to the analysis condition information, and the analysis condition information to which the environment information is added is transmitted to the server apparatus.

13. The non-transitory computer-readable recording medium according to claim 12, wherein, environment information specifying at least one of or both of temperature and humidity is generated, from sensor data output by a sensor that measures at least one of temperature and humidity around the odor sensor.

14. The non-transitory computer-readable recording medium according to claim 11, wherein, in the case where the odor analysis target originates from a user, input of personal information of the user is received, and analysis condition information further specifying the received personal information is created.

15. The non-transitory computer-readable recording medium according to claim 11, wherein the program further includes instructions that cause the computer to perform the method further comprising:

executing an application program, and when a designation of one or more odor analysis targets by the application program is received, analysis condition information specifying the designated one or more odor analysis targets is generated.

16. The non-transitory computer-readable recording medium according to claim 10, wherein, a level of the odor analysis target is estimated from the result of the analysis processing, and information indicating the estimated level is displayed on a screen, as the information indicating the result of the analysis processing.

* * * * *